United States Patent
Moreo et al.

(10) Patent No.: US 11,976,028 B2
(45) Date of Patent: May 7, 2024

(54) PROCESS FOR METHANOL PRODUCTION

(71) Applicant: Casale SA, Lugano (CH)

(72) Inventors: Pietro Moreo, Lugano (CH);
Maddalena Lepri, Cavallasca (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 16/328,470

(22) PCT Filed: Jun. 30, 2017

(86) PCT No.: PCT/EP2017/066268
§ 371 (c)(1),
(2) Date: Feb. 26, 2019

(87) PCT Pub. No.: WO2018/036693
PCT Pub. Date: Mar. 1, 2018

(65) Prior Publication Data
US 2020/0223776 A1    Jul. 16, 2020

(30) Foreign Application Priority Data
Aug. 26, 2016 (EP) ..................... 16186008

(51) Int. Cl.
| | |
|---|---|
| *C01G 49/00* | (2006.01) |
| *B01J 8/02* | (2006.01) |
| *B01J 8/04* | (2006.01) |
| *C07C 29/151* | (2006.01) |
| *C08L 57/00* | (2006.01) |
| *C08L 87/00* | (2006.01) |
| *C07C 31/04* | (2006.01) |

(52) U.S. Cl.
CPC ......... *C07C 29/1516* (2013.01); *B01J 8/0285* (2013.01); *B01J 8/0419* (2013.01); *B01J 2208/0015* (2013.01); *C07C 31/04* (2013.01)

(58) Field of Classification Search
CPC .... C07C 29/1516; B01J 8/0285; B01J 8/0419
USPC .......................................................... 568/914
See application file for complete search history.

(56) References Cited

U.S. PATENT DOCUMENTS

| | | | | |
|---|---|---|---|---|
| 4,778,662 A | * | 10/1988 | Pinto ..................... | C01C 1/0423 518/712 |
| 5,631,302 A | * | 5/1997 | Konig .................... | B01J 8/0488 252/373 |

FOREIGN PATENT DOCUMENTS

| | | | |
|---|---|---|---|
| DE | 4004862 A1 | 8/1991 | |
| RU | 2324674 C1 | 5/2008 | |
| WO | 99/59945 A1 | 11/1999 | |
| WO | WO-9959945 A1 * | 11/1999 | ......... C07C 29/1516 |
| WO | 2008/146032 A1 | 12/2008 | |
| WO | WO-2014117884 A1 * | 8/2014 | ............ B01J 8/0415 |

OTHER PUBLICATIONS

International Search Report issued in connection with PCT/EP2017/066268.
International Preliminary Report on Patentability issued in connection with PCT/EP2017/066268.

* cited by examiner

*Primary Examiner* — Yong L Chul
(74) *Attorney, Agent, or Firm* — Akerman LLP

(57) ABSTRACT

A process for the synthesis of methanol from an input stream of synthesis gas, comprising the following steps: subjecting a portion of said input stream as feed stream to an adiabatic reactive step, providing an effluent containing methanol and unreacted synthesis gas; quenching of said effluent with a further portion of said input stream, providing a quenched stream; subjecting said quenched stream to an isothermal reactive step, providing a methanol-containing product stream.

18 Claims, 3 Drawing Sheets

PROCESS FOR METHANOL PRODUCTION

This application is a national phase of PCT/EP2017/066268, filed Jun. 30, 2017, and claims priority to EP 16186008.5, filed Aug. 26, 2016, the entire contents of both of which are hereby incorporated by reference.

FIELD OF APPLICATION

The present invention relates to a process and apparatus for the synthesis of methanol.

PRIOR ART

A process for the synthesis of methanol basically comprises the production of a make-up synthesis gas by reforming of a hydrocarbon feedstock in a front-end section and the conversion of said make-up synthesis gas into methanol in a synthesis loop.

Said make-up gas is typically a mixture of carbon oxides and hydrogen with a molar ratio $(H_2-CO_2)/(CO+CO_2)$ of 2.

The conversion of the make-up gas into methanol is carried out at high temperature (200-300° C.) and pressure (40-150 bar), in the presence of an appropriate catalyst, and involves the following reactions of hydrogenation of carbon oxides (CO, $CO_2$) and reversed water-gas shift:

$CO+2H_2 \leftrightarrows CH_3OH$ $\Delta H^0{}_{298}=-90.8$ kJ/mol

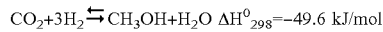
$CO_2+3H_2 \leftrightarrows CH_3OH+H_2O$ $\Delta H^0{}_{298}=-49.6$ kJ/mol

$CO_2+H_2 \leftrightarrows CO+H_2O$ $\Delta H^0{}_{298}=+41.1$ kJ/mol $\Delta H^0{}_{298}$ denotes the enthalpy change connected with a chemical reaction under standard conditions, which correspond to ambient temperature of 298.15 K (i.e. 25° C.) and an absolute pressure of 1 bar.

The global process is exothermic, reaching highest conversions at low temperatures. Hence, removal of the heat generated by the process is necessary to shift the chemical equilibrium of the process towards products, to avoid overheating and consequent damage of the catalyst.

To this purpose, a known technique is to carry out the process in a plurality of inter-cooled adiabatic catalytic beds.

An adiabatic bed comprises no means to directly cool the catalyst, which means the heat produced by the chemical process is fully transferred to the effluent. Hence, inter-bed heat exchangers are provided between consecutive beds in series in order to cool the hot effluent of a bed before its introduction to a following bed.

According to this technique, the temperature increases progressively through each bed and decreases suddenly through the subsequent inter-bed heat exchanger. However, this technique has the following drawbacks: the temperature in the catalytic bed raises with risk of formation of hot spots and the reaction equilibrium is rapidly reached entailing low yields of conversion. These problems are overcome by the isothermal reactors.

An isothermal reactor comprises a catalytic bed and heat exchange bodies immersed in said catalytic bed to remove heat directly from the bed and to keep its temperature within an optimal range. Said heat exchange bodies are generally traversed by a cooling medium such as water, which can be easily converted to steam for a further use in the plant.

Although isothermal reactors provide a more accurate temperature control and better yields of conversion, they entail a much higher investment cost than the adiabatic reactors.

Moreover, the reactor configurations above are scarcely versatile and not easily adaptable, e.g. to unstable feed compositions or to applications different from those for which they have been designed.

Hence there is a great interest in methods for the synthesis of methanol, which are efficient in terms of temperature control and yields of conversion and at the same time are flexible, able to face different situations and involving low costs. This need is particularly felt for the small scale methanol production, which also faces the complexity of treating low flowrates.

SUMMARY OF THE INVENTION

The aim of the invention is to provide a process for the synthesis of methanol, which is flexible and particularly suitable to be performed on a small scale. In particular, the invention aims at increasing the conversion yield, providing a more accurate control of the reaction temperature, reducing the volume of catalyst and maximizing the catalyst life.

These aims are reached with a process for the synthesis of methanol from an input stream of synthesis gas according to claim 1. Said process comprises the following steps:

subjecting a portion of said input stream as feed stream to an adiabatic reactive step, providing an effluent containing methanol and unreacted synthesis gas;

quenching of said effluent with a further portion of said input stream, providing a quenched stream;

subjecting said quenched stream to an isothermal reactive step, providing a methanol-containing product stream.

Said synthesis gas is a mixture of carbon oxides and hydrogen with a molar ratio between $(H_2-CO_2)$ and $(CO+CO_2)$ equal to 2.

During the adiabatic reactive step, the temperature rapidly increases providing a hot effluent and the reaction rapidly reaches the equilibrium.

Said hot effluent is then subjected to quenching. The step of quenching decreases the temperature of said hot effluent. Thanks to such temperature decrease, the reaction distances from the equilibrium and shifts to the right in the subsequent isothermal reactive step.

The term of quenching denotes mixing said hot effluent directly with a cooling medium. The hot effluent and the cooling medium are brought to direct contact and mixed together.

Said quenching is advantageously performed by mixing said hot effluent with a further portion of the input stream of synthesis gas, which has a lower temperature.

Said step of quenching is performed on said effluent after completion of the adiabatic reactive step. For example the quenching is performed downstream an adiabatic reactor. In a preferred embodiment, the effluent of an adiabatic reactor is mixed with a stream of synthesis gas downstream the adiabatic reactor.

Performing the quenching with a portion of the input stream of synthesis gas also entails a dilution of the unreacted synthesis gas in the effluent of the adiabatic reactive step and, consequently, an increased concentration of the reactants. This results in a further shift of the reaction to the right.

For ease of description said portion of synthesis gas is also referred to as a "quench stream".

The stream resulting from the mixing of the effluent of the adiabatic step and said quench stream is subjected to said isothermal reactive step during which the temperature is kept within an optimal range. Accordingly, said isothermal reactive step is carried out in a catalyst volume wherein a number of heat exchange bodies immersed therein are traversed by a suitable cooling medium to remove the heat generated by said reactive step. Said heat exchange bodies can be tubes or, preferably, plates.

Accordingly, during said isothermal reactive step, the reaction trend to equilibrium is slowed down and the temperature profile is kept close to the temperature of maximum reaction rate, until the heat absorption capacity of the cooling medium becomes lower than the generation of heat on the catalyst side. According to preferred embodiments, said cooling medium is synthesis gas.

Preferably, the feed stream to the adiabatic reactive step comprises a fraction of the input stream of synthesis gas which has been pre-heated by acting as a cooling medium of said isothermal reactive step, thus forming a pre-heated stream. Accordingly, said fraction of the input stream traverses the heat exchange bodies immersed in the catalyst volume.

More preferably, said pre-heated stream mixes with a further fraction of said input stream of synthesis to at least partially form the feed stream to the adiabatic reactive step, said further fraction being directly sent to said adiabatic reactive step. Preferably, the feed stream to the adiabatic reactive step is entirely or substantially entirely formed by mixing said pre-heated stream and said further fraction of synthesis gas.

The term "directly" is used to indicate that said further fraction of the input stream is not subjected to thermal exchange and is maintained at a substantially constant temperature.

According to different embodiments of the invention, the input stream of synthesis gas is split into two or three fractions.

In the former case, a first fraction is used for quenching the effluent of the adiabatic reactive step and a second fraction is fed to the adiabatic reactive step, either directly or after being pre-heated via passage through the above mentioned heat exchange bodies immersed in the catalyst volume wherein the isothermal reactive step takes place. Accordingly, the second fraction forms the feed stream to said adiabatic reactive step.

In the latter case, a first fraction is similarly used for quenching the effluent of the adiabatic reactive step, a second fraction is directly fed to the adiabatic reactive step and a third fraction traverses said heat exchange bodies and is heated up by absorbing the heat generated by the isothermal reactive step, thus providing a stream of preheated synthesis gas which is mixed with said second fraction to form the feed stream to the adiabatic reactive step. Preferably, said second fraction of synthesis gas has a lower temperature than said preheated synthesis gas and is referred to as "cold-shot stream". Preferably, said first fraction is not greater than the 40% (vol) of the input stream of synthesis gas. Preferably, said second fraction ranges between 5 and 30% (vol) of the input stream of synthesis gas. Preferably, said third fraction ranges between 30 and 90% (vol) of the input stream of synthesis gas.

The latter embodiment is particularly advantageous because mixing of the third fraction of preheated synthesis gas with said cold-shot stream is able to guarantee a fine regulation of the inlet temperature to the adiabatic reactive step.

According to some embodiments, said input stream of synthesis gas is obtained by pre-heating at least a portion of the effluent of the front-end section. Preferably, said at least a portion is pre-heated in a suitable heat exchanger by indirect heat exchange with the methanol-containing product stream from the isothermal reactive step.

According to a particular embodiment, said methanol-containing product stream is used to pre-heat the fraction of the input stream which is directly fed to the adiabatic reactive step when no mixing with the stream of pre-heated synthesis gas is provided.

Preferably, said adiabatic reactive step and isothermal reactive step are performed in two separate vessels.

Preferably, said step of quenching the output stream of the adiabatic reactive step with a portion of synthesis gas is carried out outside said two separate vessels.

Said process for the synthesis of methanol is particularly suitable to be performed on a small scale. The term "small scale" generally refers to a production of methanol in crude not greater than 500 BPSD (barrels per stream day), that is 63 MTPD (metric tons per day), and preferably not greater than 250 BPSD, that is 31.5 MTPD. The process of the invention can also be performed on industrial scale.

Another object of the present application is a reactor system for carrying out said process, according to the annexed claims.

The main advantage of the present invention is represented by the high variety of degrees of freedom which allows, on one hand, to maximize the performances of the process by better tuning temperatures and flowrates of the different portions of the input stream of synthesis gas and, on the other hand, to increase the adaptability of the reactor system to different conditions, for example to unstable feed compositions or to applications different from those for which the reactor system has been designed.

In particular, the possibility to set the split of the fresh synthesis gas stream into said two or three portions in order to better tune the flowrates of the cold-shot and quench streams represents one of the main degrees of freedom of the reactor system.

Accordingly, a better control of the temperature of the inlet streams to both the adiabatic and isothermal reactive steps is obtained thanks to the injection of the cold-shot and quench streams, respectively.

Another degree of freedom of the system is represented by installation of an external heat exchanger, which allows to modulate the temperatures of the portions of synthesis gas, in particular of the input stream to the adiabatic reactive step, by exchanging heat with the methanol-containing stream leaving the isothermal reactive step.

The presence of an isothermal reactor downstream of an adiabatic reactor entails: a reduction of the catalyst volume needed, because the isothermal reactor maintains the reaction conditions close to the maximum reaction rate, and the maximization of the catalyst life, because the largest portion of catalyst is loaded in the isothermal reactor, wherein the temperature peaks are much lower than the typical values of adiabatic beds.

The advantages of the invention will emerge even more clearly with the aid of the detailed description below relating to preferred embodiments.

DETAILED DESCRIPTION

Figure 1:
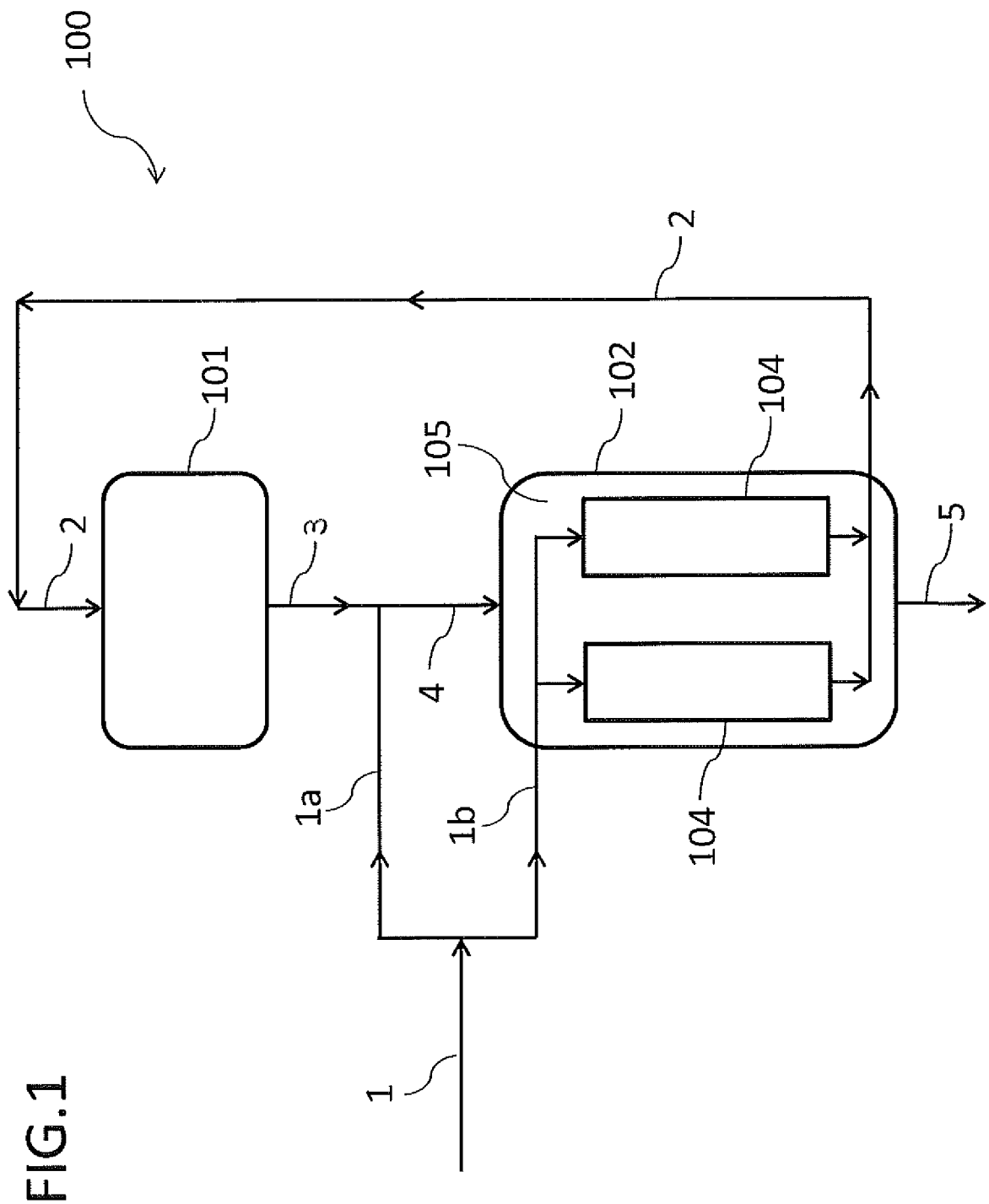
FIG. 1 illustrates a simplified scheme of a reactor system according to a first embodiment of the invention.

FIG. 1 shows a reactor system 100 for the synthesis of methanol from an input stream 1 of synthesis gas. Said input stream 1 is the effluent of a front-end section (not shown).

Said system 100 comprises a first adiabatic reactor 101 and a second isothermal reactor 102. Said first and second reactors are placed in two separate vessels. Said isothermal reactor 102 contains heat exchange plates 104 immersed in a catalytic bed 105.

Said input stream 1 of synthesis gas is split into two portions, namely a first portion 1a and a second portion 1b. Said portions 1a and 1b have the same composition, but may have different flow rates.

Said second portion 1b is used as cooling medium in the heat exchange plates 104 of the isothermal reactor 102, thus removing heat from the catalytic bed 105 and providing a stream 2 of preheated synthesis gas.

Said stream 2 of preheated synthesis gas is fed into the first adiabatic reactor 101, where partially reacts to provide an effluent stream 3 of partially reacted gas, containing methanol and unreacted synthesis gas. In said reactor 101, the temperature raises and the reaction equilibrium is rapidly reached.

Said effluent stream 3, after leaving the reactor 101, mixes with the first portion 1a of synthesis gas. Said portion 1a of synthesis gas has a lower temperature than the effluent stream 3, thus providing a stream 4 with decreased temperature and increased concentration of synthesis gas, which results in a shift of the reaction equilibrium towards rights in the subsequent isothermal reactor 102. Said first portion 1a of synthesis gas is also referred to as quench stream.

Said input stream 4 enters said isothermal reactor 102, wherein synthesis gas is further converted to methanol providing a methanol-containing product stream 5. As already described above, the heat generated during the isothermal reactive step is directly removed by the second portion 1b of synthesis gas traversing the heat exchange plates 104 immersed in the catalytic bed 105.

Figure 2:
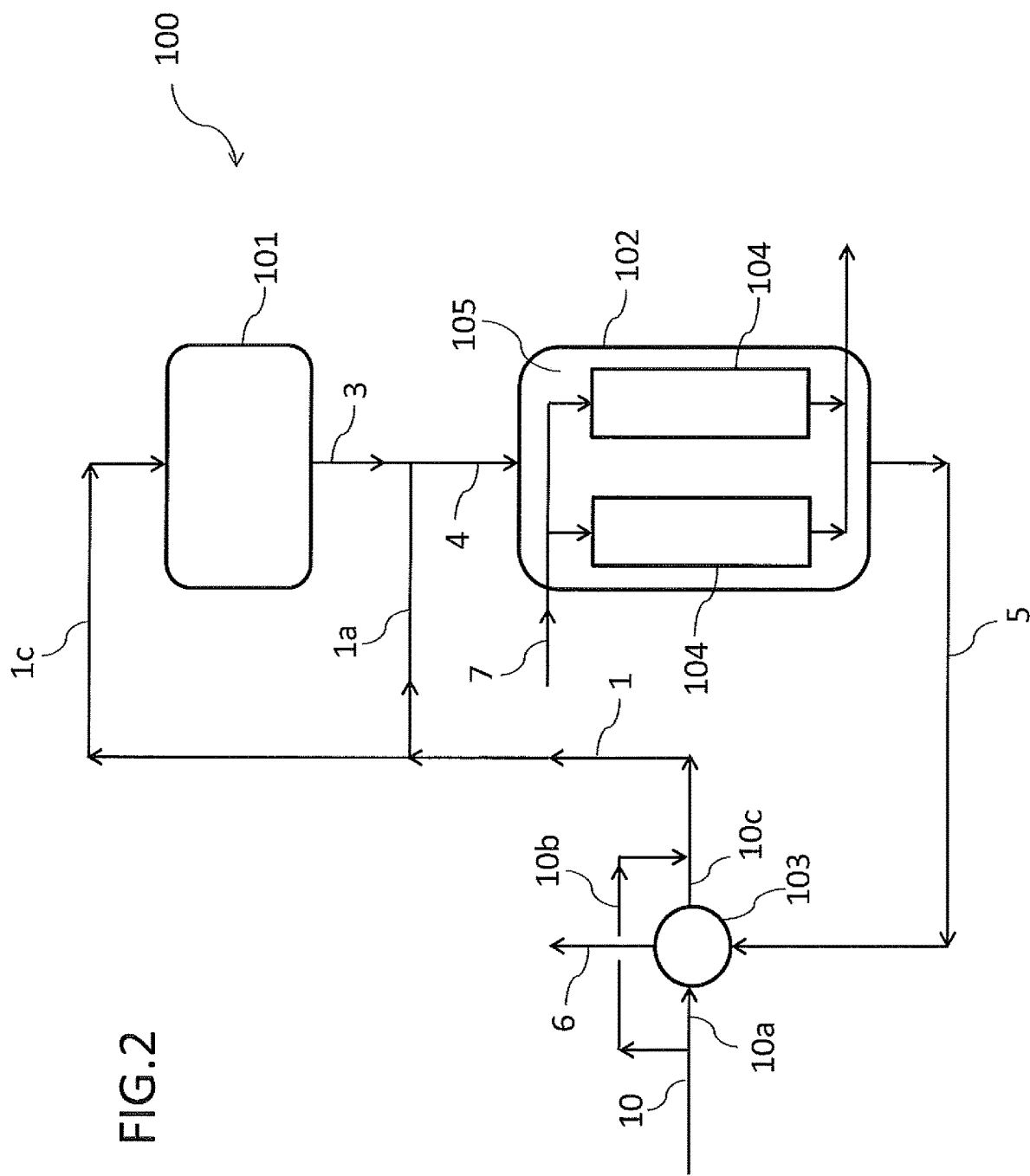
FIG. 2 illustrates a simplified scheme of a reactor system according to a second embodiment of the invention.

According to the embodiment shown in FIG. 2, the reactor system 100 comprises a heat exchanger 103, besides said first adiabatic reactor 101 and said second isothermal reactor 102.

Preferably, said input stream 1 is obtained by partially heating the effluent 10 of the front-end section (not shown). In greater detail, a portion 10a of the effluent 10 is heated in said heat exchanger 103 by heat-exchange with the methanol-containing stream 5 leaving the isothermal reactor 102 providing a pre-heated stream 10c, while the remaining portion 10b bypasses the heat exchanger 103 and merges with said pre-heated portion 10c forming the input stream 1 of synthesis gas.

Said input stream 1 of synthesis gas is split into a first portion 1a, as in the above embodiment of FIG. 1, and a second portion 1c.

Said second portion 1c forms the input stream to the first adiabatic reactor 101, where partially reacts to provide the effluent stream 3 containing methanol and unreacted synthesis gas. Said effluent stream 3 is subsequently mixed with the first portion 1a of synthesis gas having lower temperature, resulting in an input stream 4 to the isothermal reactor 102. Said input stream 4 enters the isothermal reactor 102, wherein synthesis gas is further converted to methanol forming a methanol-containing product stream 5, which is used as heating medium in the heat exchanger 103 providing a methanol-containing stream 6 with decreased temperature. Said stream 6 is subsequently subjected to purification in a suitable purification section (not shown).

According to this embodiment, the heat generated in the catalytic bed 105 of the isothermal reactor 102 is directly removed by a suitable cooling medium 7, e.g. water, traversing the heat exchange plates 104 immersed in the catalytic bed 105.

Figure 3:
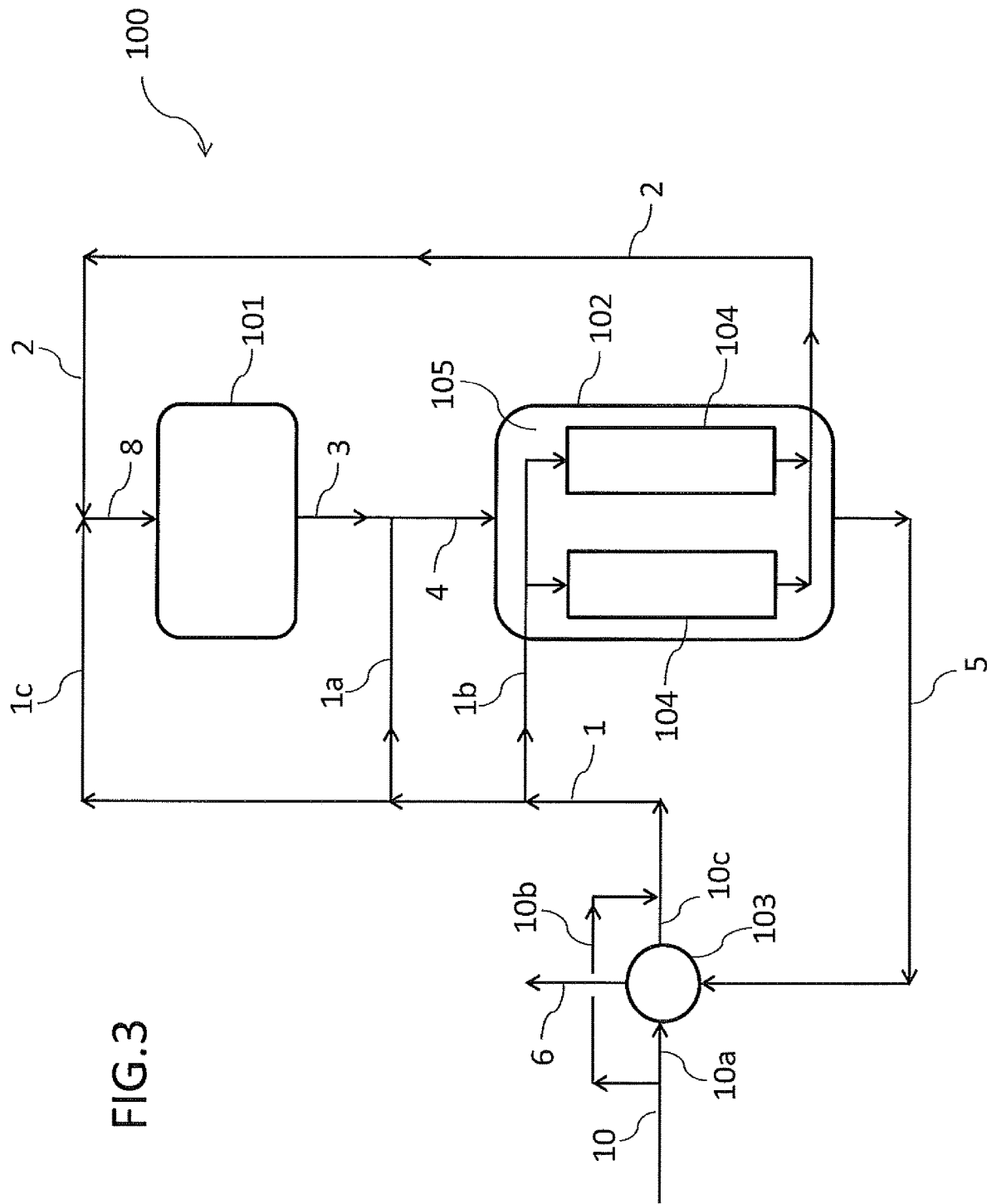
FIG. 3 illustrates a simplified scheme of a reactor system according to a third embodiment of the invention.

FIG. 3 illustrates an embodiment which is a combination of FIGS. 1 and 2, wherein the input stream 1 of synthesis gas is divided into three fractions, namely a first fraction 1a, a second fraction 1b and a third fraction 1c.

Said second fraction 1b is used as cooling medium in the heat exchange plates 104 of the isothermal reactor 102, thus removing heat from the catalytic bed 105 and providing a stream 2 of preheated synthesis gas.

Said stream 2 of preheated synthesis gas is mixed with the third fraction 1c of synthesis gas to form the input stream 8 to the adiabatic reactor 101. The third fraction 1c has lower temperature than the stream 2 and their mixing allows to finely regulate the inlet temperature to the adiabatic reactor 101. Said third fraction 1c is also referred to as cold-shot stream.

Said input stream 8 partially reacts in said adiabatic reactor 101 to provide an output stream 3 containing methanol and unreacted synthesis gas.

Said effluent stream 3 is subsequently mixed with the first fraction 1a of synthesis gas having lower temperature, resulting in an input stream 4 to the isothermal reactor 102. As a consequence, said stream 4 has a decreased temperature and an increased concentration of synthesis gas, resulting in a shift of the reaction equilibrium towards rights. Said first fraction 1a is also referred to as quench stream.

Said input stream 4 enters said isothermal reactor 102, wherein synthesis gas is further converted to methanol providing the methanol-containing stream 5. As already described above, the heat generated is directly removed by the second fraction 1b of synthesis gas traversing the heat exchange plates 104 immersed in the catalytic bed 105.

As in the embodiment of FIG. 2, the output stream 5 of the isothermal reactor 102 is used to pre-heat the portion 10a of the effluent 10 of the front-end section in the above mentioned heat exchanger 103, while the remaining portion 10b bypasses the heat exchanger 103 and merges with said pre-heated portion 10c forming the input stream 1 of synthesis gas.

The presence of said heat exchanger 103 is advantageous because allows to modulate the temperatures of the fractions 1a, 1b, 1c of synthesis gas.

What is claimed is:

1. A process for the synthesis of methanol from an input stream of synthesis gas, comprising the following steps:
    subjecting a portion of said input stream as feed stream to an adiabatic reactive step, providing an effluent containing methanol and unreacted synthesis gas;
    quenching of said effluent with a further portion of said input stream, providing a quenched stream;
    subjecting said quenched stream to an isothermal reactive step, providing a methanol-containing product stream;
    wherein said isothermal reactive step is carried out in a catalytic bed comprising heat exchange bodies.

2. The process according to claim 1, wherein the feed stream to said adiabatic reactive step comprises a fraction of said input stream which has been pre-heated by acting as a cooling medium of said isothermal reactive step, thus forming a pre-heated stream.

3. The process according to claim 2, wherein said pre-heated stream mixes with a further fraction of said input stream to form the feed stream to said adiabatic reactive step, said further fraction being directly sent to said adiabatic reactive step.

4. The process according to claim 2, wherein said fraction acting as cooling medium traverses said heat exchange bodies.

5. The process according to claim 1, wherein said input stream is obtained by pre-heating at least a portion of a stream of synthesis gas by indirect heat exchange with said methanol-containing product stream.

6. The process according to claim 1, which is suitable to be performed on a small scale.

7. A reactor system for the synthesis of methanol from an input stream of synthesis gas, comprising:
   an adiabatic catalytic zone, receiving a portion of said input stream as feed stream, and providing an effluent containing methanol and unreacted synthesis gas;
   a quench line of a further portion of said input stream which mixes with said effluent, providing a quenched stream;
   an isothermal catalytic zone, receiving said quenched stream and providing a methanol-containing product stream;
   said isothermal catalytic zone comprising a catalytic bed and heat exchange bodies immersed in the catalytic bed.

8. The reactor system according to claim 7, wherein said feed stream to the adiabatic catalytic zone comprises a stream of pre-heated synthesis gas and said reactor system comprises a line for feeding a fraction of said input stream into said heat exchange bodies to act as a cooling medium, thus providing said stream of pre-heated synthesis gas.

9. The reactor system according to claim 8, wherein said feed stream to the adiabatic catalytic zone comprises a further fraction of synthesis gas which is directly sent to the adiabatic zone and said reactor system comprises a line for mixing said further fraction with said stream of pre-heated synthesis gas.

10. The reactor system according to claim 7, wherein said input stream is obtained by pre-heating at least a portion of a stream of synthesis gas and said reactor system comprises a heat exchanger receiving the methanol-containing product stream as heating medium to pre-heat said at least a portion of said stream of synthesis gas and provide said input stream.

11. The reactor according to claim 7, wherein said adiabatic zone comprises a single catalytic bed.

12. The reactor system according to claim 7, wherein said adiabatic zone and said isothermal zone are comprised in separate reaction vessels.

13. The reactor system according to claim 12, wherein the quench line of said further portion of the input stream is injected into the effluent of the adiabatic catalytic zone outside said separate vessels.

14. The process according to claim 6, wherein the process is suitable to produce methanol in crude not greater than 500 barrels per stream day (or 63 metric tons per day).

15. The reactor system according to claim 7, wherein water is fed to the heat exchange bodies as a cooling medium.

16. The reactor system according to claim 10, wherein a portion of the steam of synthesis gas bypasses said heat exchanger and merges with said pre-heated portion of the stream of synthesis gas forming the input stream.

17. The process according to claim 3, wherein said further portion of said input steam for quenching the effluent of said adiabatic reactive step is not greater than 40% (vol) of said input stream, said further fraction of said input stream for mixing with said pre-heated stream ranges between 5 and 30% (vol) of said input stream, and said fraction of said input stream which is pre-heated by acting as cooling medium of said isothermal reactive step ranges between 30 and 90% (vol) of said input stream.

18. The reactor system according to claim 7, said heat exchange bodies being plates.

* * * * *